US009395339B2

United States Patent
Sarr et al.

(10) Patent No.: US 9,395,339 B2
(45) Date of Patent: Jul. 19, 2016

(54) APPARATUS FOR NON-DESTRUCTIVE INSPECTION OF STRINGERS

(71) Applicants: Dennis P. Sarr, Kent, WA (US); Hien T. Bui, Renton, WA (US)

(72) Inventors: Dennis P. Sarr, Kent, WA (US); Hien T. Bui, Renton, WA (US)

(73) Assignee: The Boeing Comapany, Chicago, IL (US)

( * ) Notice: Subject to any disclaimer, the term of this patent is extended or adjusted under 35 U.S.C. 154(b) by 339 days.

(21) Appl. No.: 13/975,599

(22) Filed: Aug. 26, 2013

(65) Prior Publication Data

US 2015/0053015 A1    Feb. 26, 2015

(51) Int. Cl.
| | |
|---|---|
| *G01N 29/265* | (2006.01) |
| *G01N 29/06* | (2006.01) |
| *G01N 29/24* | (2006.01) |
| *G01N 29/22* | (2006.01) |

(52) U.S. Cl.
CPC .............. *G01N 29/24* (2013.01); *G01N 29/225* (2013.01); *G01N 29/265* (2013.01); *G01N 2291/0231* (2013.01); *G01N 2291/2694* (2013.01)

(58) Field of Classification Search
CPC ... G01N 29/24; G01N 29/225; G01N 29/265; G01N 29/2493; G01N 29/28; G01N 29/2487; G01N 29/0645; G01N 29/043; G01N 29/041
USPC .................... 73/632–635, 639–644, 618–620
See application file for complete search history.

(56) References Cited

U.S. PATENT DOCUMENTS

| | | | |
|---|---|---|---|
| 4,807,476 A | * | 2/1989 | Cook ................. G01N 29/0645 73/620 |
| 6,658,939 B2 | | 12/2003 | Georgeson et al. |
| 7,249,512 B2 | | 7/2007 | Kennedy et al. |
| 7,448,271 B2 | | 11/2008 | Duncan et al. |
| 7,516,664 B2 | | 4/2009 | Meier et al. |
| 7,617,732 B2 | | 11/2009 | Bui et al. |
| 7,698,947 B2 | | 4/2010 | Sarr |

(Continued)

FOREIGN PATENT DOCUMENTS

| | | |
|---|---|---|
| CN | 202649174 U | 1/2013 |
| JP | 2011252759 A | 12/2011 |

OTHER PUBLICATIONS

Sanz et al., "Robotized Inspection System of the External Aircraft Fuselage Based on Ultrasound", The 2010 IEEE/RSJ Int'l Conf. on Intelligent Robots and Systems, Oct. 18-22, 2010, Taipei, Taiwan, pp. 2612-2617.

(Continued)

*Primary Examiner* — Helen Kwok
(74) *Attorney, Agent, or Firm* — Ostrager Chong Flaherty & Broitman P.C.

(57) ABSTRACT

A multi-sensor NDI probe having means for self-alignment of the NDI sensors in conjunction with the movement of the sensor suite along the length of a hollow elongated stiffener having a rounded cap. The apparatus comprises a large-radius curved ultrasonic transducer array with cylindrical focus, which provides complete coverage for the rounded cap, two small-radius convex curved transducer arrays for NDI of the lower outside radii, and two linear transducer arrays for NDI of the sides of the stiffener. The five transducer arrays are supported by respective compliant assemblies which facilitate proper adjustment of the location (i.e., position and orientation) of the transducer arrays during scanning. The positions of the transducer arrays are adjusted to account for geometric variations in the stiffener.

17 Claims, 15 Drawing Sheets

(56) References Cited

U.S. PATENT DOCUMENTS

| | | | | |
|---|---|---|---|---|
| 7,836,768 | B2* | 11/2010 | Young | G01N 29/041 73/620 |
| 8,082,793 | B2 | 12/2011 | Sarr et al. | |
| 8,219,245 | B2 | 7/2012 | Merk et al. | |
| 8,234,942 | B2 | 8/2012 | Sarr et al. | |
| 8,333,115 | B1 | 12/2012 | Garvey et al. | |
| 2006/0042391 | A1* | 3/2006 | Georgeson | G01N 29/07 73/633 |
| 2006/0162456 | A1* | 7/2006 | Kennedy | G01N 29/225 73/620 |
| 2006/0243051 | A1* | 11/2006 | Bui | G01N 29/043 73/618 |
| 2007/0062290 | A1 | 3/2007 | Roh et al. | |
| 2010/0095775 | A1* | 4/2010 | Sarr | G01N 29/265 73/621 |

OTHER PUBLICATIONS

Partial European Search Report, European Application No. 14180808.9 (European counterpart to the instant application), dated Feb. 11, 2015 [sic].

Extended European Search Report, European Application No. 14180808.9 (European counterpart to the instant application), dated Jul. 14, 2015.

Canadian Office Action dated Oct. 30, 2015 in Canadian Application No. 2,856,683 (Canadian counterpart to the instant patent application).

* cited by examiner

APPARATUS FOR NON-DESTRUCTIVE INSPECTION OF STRINGERS

BACKGROUND

This disclosure generally relates to non-destructive inspection equipment and methods, and relates more particularly to methods and apparatus for inspecting structures made of composite material.

Non-destructive inspection of structures involves thoroughly examining a structure without harming the structure or requiring its significant disassembly. Non-destructive inspection is commonly used in the aircraft industry to inspect aircraft structures for any type of internal or external damage to or flaws in the structure. Non-destructive inspection is also used in the initial fabrication of the aircraft's structural components. It is used to assure that a part was fabricated correctly and that foreign material is not embedded within the part. Inspection may be performed during manufacturing of a structure and/or after a structure has been put in service Non-destructive inspection (NDI) may be performed on stiffened composite parts of an aircraft. The stiffener of the stiffened part may be made of a composite material such as carbon fiber-reinforced plastic (CFRP). A composite stringer attached to a composite fuselage is but one example of such a stiffener.

The quality of a stiffened part can be determined non-destructively by ultrasonic testing. A stiffened part can be inspected ultrasonically by a probe including one or more shoes that hold respective ultrasonic transducer arrays. During NDI, the shoes are pressed against respective external surfaces of the stiffened part, the transducers are acoustically coupled to the stiffened part (e.g., using water), and the probe is moved incrementally along the length of the stiffened part. As the probe is being moved, the transducer arrays operate in pulse/echo mode to generate pulsed ultrasonic waves, which propagate into the stiffened part. Reflected ultrasonic waves are returned to and detected by the transducer arrays to provide data indicative of the presence of cracks, voids, delaminations, etc. in the stiffened part. Data acquired by the transducer arrays is typically processed by a computer system, and the processed data may be presented to a user via a computer monitor. A data acquisition device and data handling software may be used for collection and display of inspection data, such as displaying the data on a computer monitor as an image representation of the structure under inspection, such as a hat stringer, supplemented with corresponding color and/or graphical data of the inspection to permit examination by a qualified inspector.

A typical NDI probe has sensing elements, such as ultrasonic transducers, which are placed in proximity to the surface to be inspected. In many cases, the inspected part has multiple surfaces of different shapes and orientations, requiring the use of multiple transducer arrays. This enables the inspection of the structure to proceed more rapidly and efficiently, thereby reducing the costs associated with the inspection. Typically, different structures are inspected using respective transducer arrays which have been specifically designed to provide transducer alignment (position and orientation with respect to the surfaces of the structure) and scan coverage for the entire structure.

The aerospace industry has been moving from manual manufacturing by skilled workers to the use of automated machinery. This is particularly the case in the field of non-destructive inspection of composite structures. Automated inspection systems have been developed as an alternative to manual and semi-automated inspection techniques. Such systems typically employ a manipulator (e.g., overhead gantry, multi-axis scanner, or robot) that scans the NDI end effector along the part being inspected. For single-sided inspection methods, such as pulse echo ultrasonic inspection, a single-arm robotic device having six degrees of freedom may be used to position and move an NDI end effector, such as a pulse echo ultrasonic inspection device, attached to the end of the robot arm. The part to be inspected may be mounted to a holder which is rotatable about an axis. Thus a total of eight degrees of freedom allow for complete inspection of the part. The eight degrees of freedom are controlled by a robot controller in accordance with trajectories generated from a digital model of the inspected part.

Various systems have been employed for inspecting fuselage and wingbox stiffeners (also known as "hat stringers") having a trapezoidal profile with two corner radii. Some systems have three transducers which are respectively employed to inspect the corners and a central cap portion connecting the corners. Each transducer has its own ultrasonic setup technique and its own NDI qualification that it has to meet. Data from three transducer arrays has to be stitched together to provide a continuous C scan data display. Such three-transducer systems for inspecting a stringer cap may have a large, expensive and complex configuration and are not optimal for inspecting rounded cap stringers.

The foregoing systems may be further equipped with four transducer arrays for NDI of the lower outside radii (LOR) and stringer sides (SS). In such seven-transducer systems, the robot will keep the three transducer arrays that scan the cap and corners aligned, but the other transducer arrays for the LOR and SS are subject to many dimensional factors that hinder their positioning. They must be able to adapt to the following variables: stringer height, stringer thickness, fuselage ply drops, asymmetrical stringer cross section, and irregular surface conditions due to process problems (porosity, resin bubbles, etc.). If the LOR and SS transducer arrays are unable to adequately adjust to the foregoing variables, it may become necessary to perform a rescan.

It would be advantageous to provide a self-aligning automated system for inspecting a rounded cap stiffener in a single continuous NDI procedure while reducing or eliminating rescan of the stiffeners.

SUMMARY

The subject matter disclosed in detail below is directed to multi-sensor NDI systems having means for self-alignment of the NDI sensors in conjunction with the movement of the sensor suite along the length of a hollow elongated structure having a rounded cap (hereinafter "rounded structure"). For purposes of illustration, embodiments will be described in which the NDI sensors are respective ultrasonic transducer arrays and the rounded structure is a rounded cap stringer attached to a fuselage. However, the teachings herein have application to other rounded structures and any other type of sensor suited for NDI of composite material.

An apparatus is provided for NDI of a large-radius composite structure (made, e.g., of graphite epoxy), such as a fuselage stringer that has a rounded configuration. In accordance with embodiments disclosed herein, the apparatus comprises a large-radius curved ultrasonic transducer array (e.g., 64 transducer elements) with cylindrical focus, which provides complete coverage for the so-called "cap" of the rounded cap stringer. This transducer array has adjustment in height and in the axial direction of the stringer for optimum set-up. By using this optimum set-up and time-corrected gain, the rounded cap of a composite stringer can be non-destructively inspected without adjusting or changing the set-up. In particular, the design of the apparatus allows one set-up to be used for scanning a cap of a rounded cap stringer with ply changes (e.g., from five to twelve plies). This avoids having to adjust the gain or have multiple NDI procedures for NDI of the cap. It also reduces the number of transducers from three to one when inspecting the cap of a stringer. In accordance with one implementation, this probe uses stainless steel mechanical slides for precise alignment for keeping the normality of the transducer array relative to the stringer. The probe also has a reduced water column for reduction of water flow in a bubbler configuration. This probe configuration can be used in any orientation for ease of scanning of a composite part. This probe allows NDI of a stringer without having to rotate the composite structure.

In addition to having a large-radius concave curved transducer array for NDI of the upper cap radius (UCR) of a rounded cap stringer, the embodiments disclosed herein further comprise two small-radius convex curved transducer arrays for NDI of the lower outside radii (LOR) and two linear transducer arrays for NDI of the stringer sides (SS). The five transducer arrays are supported by respective compliant assemblies which facilitate proper adjustment of the location (i.e., position and orientation) of the transducer arrays. The respective transducer arrays and their compliant support apparatus will be referred to herein as transducer assemblies. The UCR transducer assembly is pivotably coupled to a yoke, which yoke in turn is attached to a main structure plate. The LOR and SS transducer assemblies are mounted at respective corners of the main structure plate. The yoke and main structure plate are both connected to a robot interface plate/assembly.

During NDI of a rounded cap stringer, the robot will keep the UCR transducer array aligned. The LOR and SS transducer assemblies disclosed herein are able to adapt to the above-discussed variations in stringer dimensions, fuselage ply drops, unsymmetrical stringer cross sections, and irregular surface conditions due to process problems (porosity, resin bubbles, etc.). More specifically, the LOR and SS transducer assemblies comprise built-in centering mechanisms that enable the LOR and SS transducer arrays to adapt to the foregoing variables.

One aspect of the subject matter disclosed herein is an apparatus comprising: a support structure; a large shaft pivotably and slidably coupled to the support structure; a flexible coupling attached to one end of the large shaft; a transducer holder attached to the flexible coupling; a transducer array held by the transducer holder; and a centering mechanism attached to the transducer holder.

In accordance with one implementation, the centering mechanism comprises: first and second small shafts supported at opposite ends thereof by the transducer holder; first and second pivot/slide mechanisms slidably coupled to the first and second small shafts respectively; and first and second four-link centering guide assemblies pivotably coupled to the first and second pivot/slide mechanisms respectively. The first pivot/slide mechanism comprises a first bearing and a first pivot pin, while the second pivot/slide mechanism comprises a second bearing and a second pivot pin, the first and second small shafts being slidable in the first and second bearings respectively, and the first and second four-link centering guide assemblies being pivotably coupled to the first and second pivot pins respectively. Each of the first and second four-link centering guide assemblies comprises first and second upper centering guides pivotably coupled to the first and second pivot/slide mechanisms respectively and first and second lower centering guides respectively pivotably coupled to the first and second upper centering guides and pivotably coupled to each other. The centering mechanism further comprises respective pluralities of rolling elements rollably coupled to the first and second lower centering guides. The transducer array is disposed between the first and second four-link centering guide assemblies.

Another aspect of the disclosed subject matter is an apparatus comprising: a first support structure having an axis, the first support structure comprising a plate disposed perpendicular to the axis and first through fourth sleeves fixedly coupled to the plate and disposed at respective corners of a rectangle; first through fourth bearings seated in the first through fourth sleeves respectively; first through fourth large shafts pivotably and displaceably coupled to the first through fourth bearings respectively; first through fourth flexible couplings respectively attached to respective ends of the first through fourth large shafts; first through fourth transducer holders respectively attached to the first through fourth flexible couplings; first through fourth transducer arrays respectively attached to the first through fourth transducer holders; and first through fourth centering mechanisms respectively attached to the first through fourth transducer holder.

In accordance with one implementation, each of the first through fourth centering mechanisms comprises: first and second small shafts supported at opposite ends thereof by a respective one of the first through fourth transducer holders; first and second pivot/slide mechanisms slidably coupled to the first and second small shafts respectively; and first and second four-link centering guide assemblies pivotably coupled to the first and second pivot/slide mechanisms respectively. Each of the first pivot/slide mechanisms respectively comprises a first bearing and a first pivot pin, and each of the second pivot/slide mechanisms respectively comprises a second bearing and a second pivot pin, the first and second shafts being slidable in the first and second bearings respectively, and the first and second four-link centering guide assemblies being pivotably coupled to the first and second pivot pins respectively. Each of the first and second four-link centering guide assemblies comprises first and second upper centering guides pivotably coupled to the first and second pivot/slide mechanisms respectively and first and second lower centering guides respectively pivotably coupled to the first and second upper centering guides and pivotably coupled to each other. Each of the first and second transducer arrays has a concave curvature, each of the third and fourth transducer arrays is linear, and the first through fourth transducer arrays are arranged so that when the first transducer array confronts a first outer radius of a stiffener, the second transducer array will confront a second outer radius of the stiffener, the third transducer array will confront a first side of the stiffener, and the fourth transducer array will confront a second side of the stiffener.

The apparatus may further comprise: a second support structure fixedly coupled to the second support structure plate of the first support structure; a fifth transducer holder pivotably coupled to the second support structure; and a fifth transducer array held by the fifth transducer holder, wherein the fifth transducer array has a concave curvature of sufficient length to enable interrogation of a rounded cap of the stiffener when the first transducer array confronts the first outer radius of the stiffener.

A further aspect is a system comprising: a skin structure; a stiffener attached to the skin structure, wherein the stiffener is made of composite material and comprises a cap, first and second sides connected to the cap, and first and second lower outer radii connected to the first and second sides respectively; a manipulator comprising an arm; and an ultrasonic inspection probe coupled to the arm. The ultrasonic inspection probe comprises: a probe support structure coupled to the arm of the manipulator, the probe support structure comprising a plate first through fourth support elements fixedly coupled to the plate and disposed at respective corners of a rectangle; and first through fourth transducer assemblies pivotably and displaceably coupled to the first through fourth support elements, each of the first through fourth transducer assemblies comprising a respective transducer holder, a respective transducer array held by a respective transducer holder, and a respective centering mechanism attached to a respective transducer holder. The transducer arrays of the first and second transducer assemblies have a concave curvature and are respectively acoustically coupled to the first and second lower outer radii of the stiffener, while the transducer arrays of the third and fourth transducer assemblies are linear and are respectively acoustically coupled to the first and second sides of the stiffener.

The system described in the preceding paragraph may further comprise a fifth transducer assembly pivotably coupled to the probe support structure, the fifth transducer assembly comprising a transducer array acoustically coupled to the rounded cap of said stiffener, the fifth transducer array having a concave curvature of sufficient length to enable interrogation of the rounded cap from at or near the first side to at or near the second side of the stiffener.

Yet another aspect is a system comprising: a skin structure; a stiffener attached to the skin structure, wherein the stiffener is made of composite material and comprises a rounded cap, first and second sides connected to the rounded cap, and first and second lower outer radii connected to the first and second sides respectively; a manipulator comprising an arm; and an ultrasonic inspection probe coupled to the arm. The ultrasonic inspection probe comprises: a probe support structure coupled to the arm of the manipulator; and a first transducer assembly pivotably coupled to the probe support structure, the first transducer assembly comprising a first transducer array acoustically coupled to the rounded cap of the stiffener. The first transducer array having a concave curvature of sufficient length to enable interrogation of the rounded cap from at or near the first side to at or near the second side of the stiffener. In one implementation the probe support structure comprises a main structure plate coupled to the arm of the manipulator and a yoke attached to the main structure plate, and the first transducer array is pivotably coupled to the yoke.

The system may further comprise a second transducer assembly comprising a large shaft pivotably and slidably coupled to the probe support structure, a flexible coupling attached to one end of the large shaft, a transducer holder attached to the flexible coupling, a second transducer array held by the transducer holder, and a centering mechanism attached to the transducer holder. In one implementation, the centering mechanism comprises: first and second small shafts supported at opposite ends thereof by the transducer holder; first and second pivot/slide mechanisms slidably coupled to the first and second shafts respectively; and first and second four-link centering guide assemblies pivotably coupled to the first and second pivot/slide mechanisms respectively. The second transducer array may have a concave curvature and be acoustically coupled to the first lower outer radius of the stiffener, or the second transducer array is linear and acoustically coupled to the first side of the stiffener. A total of five transducer arrays may be provided for NDI of the rounded cap, the sides and the lower outer radii of a stiffener.

Other aspects of systems and methods for NDI of a rounded cap stiffener are disclosed below.

BRIEF DESCRIPTION OF THE DRAWINGS

Reference will hereinafter be made to the drawings in which similar elements in different drawings bear the same reference numerals.

DETAILED DESCRIPTION

Embodiments of non-destructive inspection apparatus and methods for inspecting rounded cap composite stringers for an aircraft fuselage will now be described. However, the apparatus and methods disclosed herein may also be used for similar applications which require non-destructive inspection, including other elongated composite stiffeners having a rounded cap.

Inspecting hat stringers normally requires a one-sided inspection technique, such as pulse echo ultrasonic (PEU) inspection. However, the shapes of hat stringers complicate the inspection. The hat stringer inspection devices disclosed herein are capable of performing pulse echo inspection on hat stringers that have a rounded profile when viewed in cross section. The disclosed embodiments are configured to scan both sides and the top section of a hat stringer to permit single-pass inspection. The transducer array are strategically placed and oriented to ensure full inspection of the entire hat stringer. Support structures for inspection sensors, also referred to as transducer holders, may be fabricated for specific placement and orientation of transducer arrays corresponding to the intended shapes and sizes of hat stringers.

Figure 1:
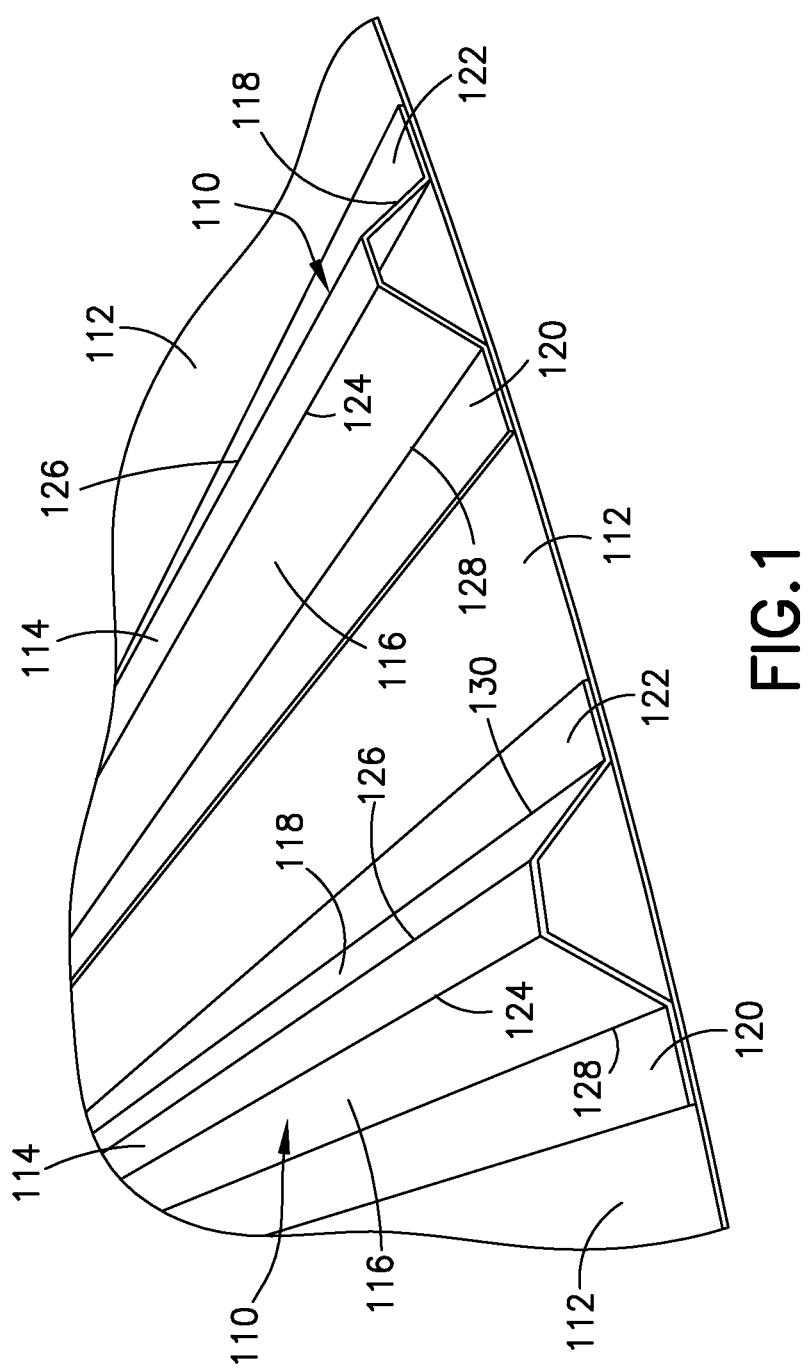
FIG. 1 is a diagram representing a perspective view of a structure comprising trapezoidal stringers attached to a skin.

FIG. 1 is a perspective view of a structure with two hat stringers 110. The structure includes a skin 112 to which individual or connected hat stringers 110 are attached to stiffen the overall structure. Each hat stringer 110 is a trapezoidal structure comprising angled sides 116 and 118 which connect to a cap 114 at corners 124 and 126 respectively. Each hat stringer 110 is affixed to the skin 112 at flanges 120 and 122, which connect to the angled sides of the hat stringer at respective corners 128 and 130. In order to inspect hat stringers having the structure shown in FIG. 1, one approach is known using a suite of seven transducer arrays: one to inspect a central cap portion 114; two to inspect angled sides 116 and 118; two to inspect cap corners 124 and 126; and two to inspect corners 128 and 130. It should be understood that the term "corner" as used herein refers to a radiused surface. The central cap portion 114 may be a planar surface connecting the cap corners 124 and 126.

In accordance with the teachings herein, an apparatus is provided for inspecting a stringer having a rounded cap (hereinafter "rounded cap stringer), meaning that the angled sides of the stringer are connected by means of a continuously curved cap. For example, the profile of the continuously curved cap may be a section of a circular, elliptical, parabolic, or other type of curved line.

Figure 2:
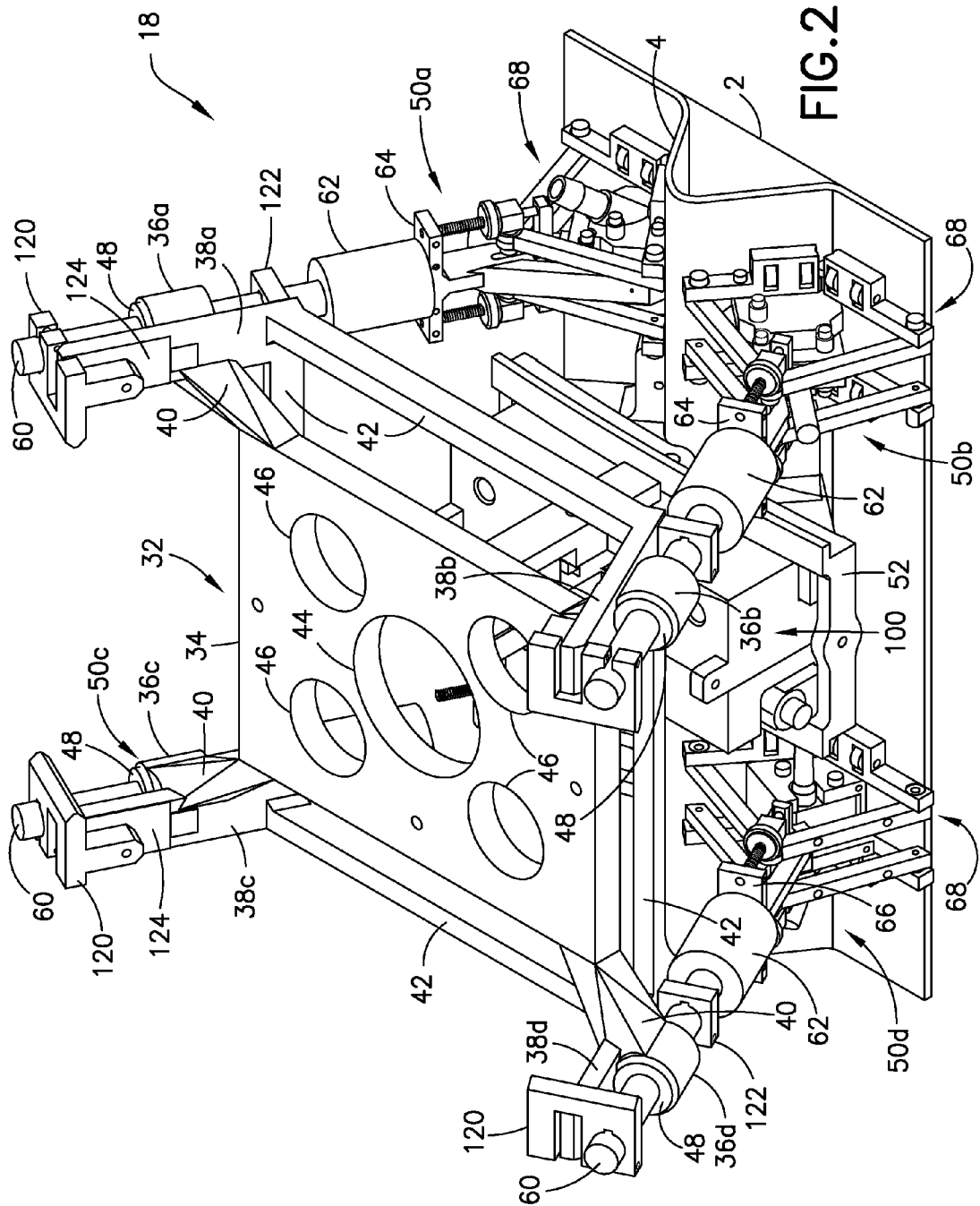
FIG. 2 is a diagram representing one view extracted from a digital model of an NDI probe seated on a rounded cap stiffener in accordance with one embodiment.

FIG. 2 depicts an ultrasonic inspection probe 18 seated on a rounded cap stringer 4 in accordance with one embodiment. The rounded cap stringer 4 is attached to and serves to stiffen a skin structure 2 (e.g., a fuselage skin). The rounded cap stringer 4 is made of composite material and comprises a cap, first and second angled sides connected to the cap, and first and second lower outer radii connected to the first and second sides respectively. The probe 18 may be mounted on an arm of a computer-controlled manipulator (not shown) for scanning the rounded cap stringer 4 in a lengthwise direction (assuming, for the purpose of illustration, that the elongated rounded cap stringer 4 is straight).

In accordance with the embodiment depicted in FIG. 2, the ultrasonic inspection probe 18 comprises a probe support structure 32 coupled to the manipulator arm (nor shown), four transducer assemblies 50a-50d pivotably and displaceably coupled to the probe support structure 32. The probe support structure 32 comprises a rectangular main structure plate 34 and four support sleeves 36a-36d on respective support legs 38a-38d. The support legs 38a-38d are connected to respective corners of main structure plate 34 by respective corner beams 40 and are connected to adjacent support legs by a plurality (i.e., four) side beams 42. The main structure plate 34 has a large circular central hole 44 and four smaller circular corner holes 46.

In the embodiment depicted in FIG. 2, the main structure plate 34, support sleeves 36a-36d, support legs 38a-38d, corner beams 40, and side beams 42 are integrally formed as one monolithic part. However, the probe support structure 32 could be readily assembled from individually formed parts.

As seen in FIG. 2, the transducer assemblies 50a-50d are pivotably and displaceably coupled to support sleeves 36a-36d by means of respective sleeve bearings 48. The transducer assemblies 50a and 50b (hereinafter "SS transducer assemblies") comprise respective linear transducer arrays (not visible in FIG. 2) positioned for interrogating the respective angled sides of the rounded cap stringer 4; the transducer assemblies 50c and 50d (hereinafter "LOR transducer assemblies") comprise respective transducer arrays (not visible in FIG. 2) having a concave curvature and positioned for interrogating the respective lower outer radii of the rounded cap stringer 4. To facilitate such interrogation, the transducer arrays 50a-50d are acoustically coupled to confronting portions of the rounded cap stringer 4 by water supplied into respective water columns (not visible in FIG. 2) which separate the transducer arrays from the rounded cap stringer 4 during inspection.

The probe 18 further comprises a transducer assembly 100 (hereinafter "UCR transducer assembly") which is pivotable relative to probe support structure 32. (Only portions of UCR transducer assembly 100 are shown in FIG. 2.) The UCR transducer assembly 100 comprises a transducer array (not visible in FIG. 2) which is positioned to enable acoustic coupling with the rounded cap of the stringer 4. The UCR transducer array 100 has a concave curvature of sufficient length to enable interrogation of the rounded cap from at or near one angled side of the stringer 4 to at or near the other angled side.

In the embodiment depicted in FIG. 2, the UCR transducer assembly 100 is pivotably coupled to a cradle 52. The cradle 52 is attached to a cross bar (not shown in FIG. 2), which is in turn attached to the main structure plate 34. (More details concerning the cradle and cross bar, which form a yoke, will be provided later with reference to FIG. 9.)

Figure 3:
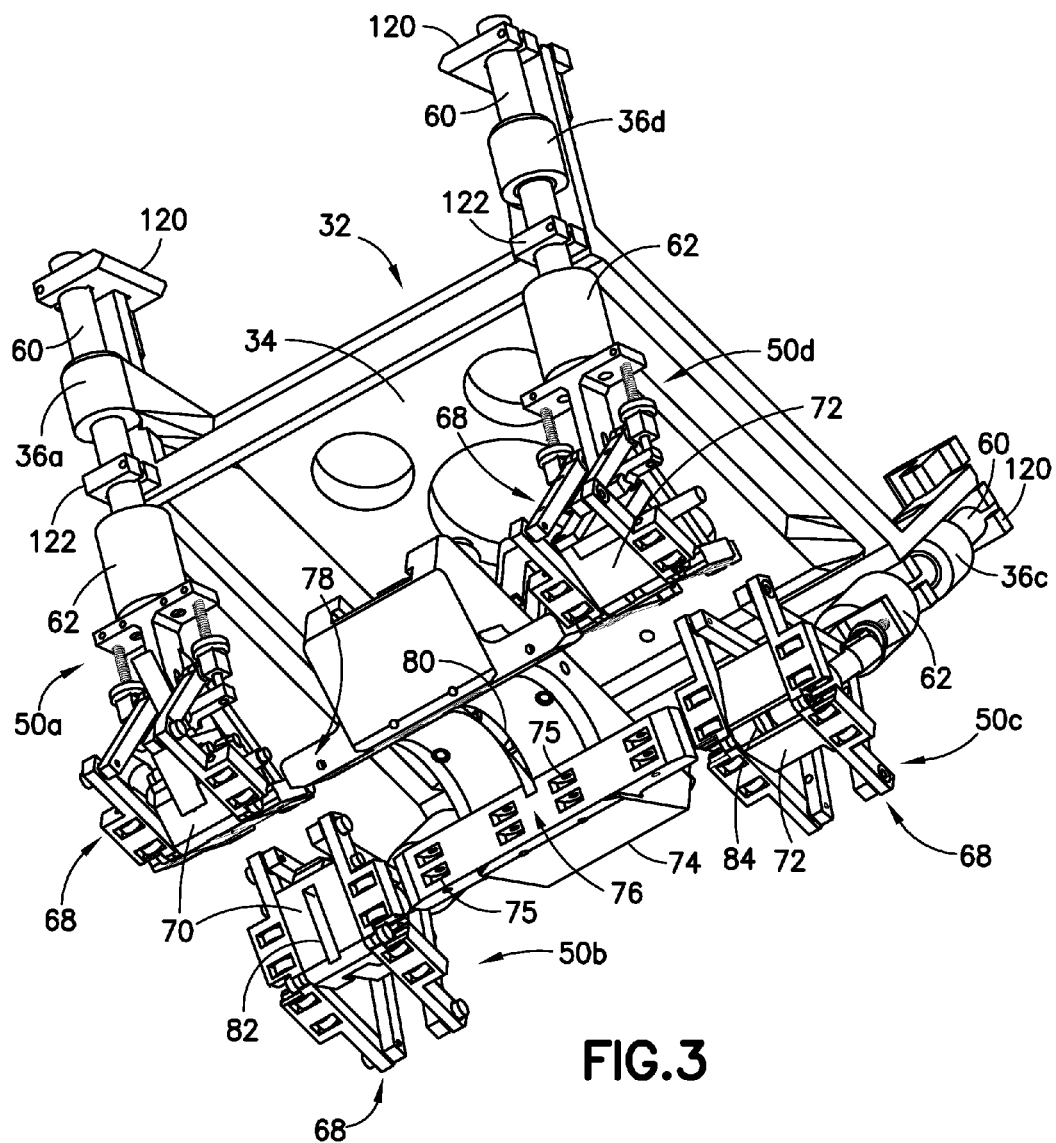
FIG. 3 is a diagram representing another view from the same digital model from which FIG. 2 was extracted as seen from a vantage point below the probe.

FIG. 3 is another view from the same digital model from which FIG. 2 was extracted, but seen from a vantage point below the probe. The aforementioned cradle is omitted from FIG. 3, and the only components of the UCR transducer assembly shown in FIG. 3 is the lower housing 74. The lower housing comprises a pair of rolling members 76 and 78 disposed at angles designed to match the angles of the angled sides of the rounded cap stiffener being inspected. Each rolling member 76, 78 comprises a respective multiplicity of bearing wells 75. The roller bearings which would be rotatably mounted in bearing wells 75 by means of shafts are not shown. The roller bearings are positioned so that they will roll in parallel on respective angled sides of the rounded cap stiffener as the probe moves along the stiffener. The bottom surface of the lower housing 74 has a rounded shape that allows the lower housing 74 to travel along the rounded cap stringer. The lower housing 74 comprises a water column 80, which is situated below a concave curved transducer array (not visible in FIG. 3) for inspecting the upper cap radius as the rolling bearings roll on the angled sides of the stiffener.

Returning attention to FIG. 2, each of the transducer assemblies 50a-50d comprises a respective shaft 60 which is displaceable along and pivotable about its own axis relative to the probe support structure 32. Each shaft 60 slides and rotates in a respective sleeve bearing 48. The shafts 60 are coupled to the respective centering mechanisms 68 by means of a respective flexible coupling 62 and a respective transducer holder 64 or 66. Each flexible coupling 62 may take the form of an aluminum rod having a spiral slot cut through the length of the aluminum tube to form a helical coil in a center section that acts as a spring. The flexure allowed by the center portion of the coupling accommodates angular, parallel and axial misalignment between the attached shafts 60 and transducer holders 64 or 66. Such a flexible coupling is commercially available from Lovejoy, Inc., Downers Grove, Ill.

The transducer assemblies 50a-50d will now be described in more detail with reference to FIGS. 4 and 5, which are elevational views of opposite ends of the NDI probe depicted in FIG. 2. One end of the probe (shown in FIG. 4) is equipped with a pair of transducer assemblies 50a, 50b which compliantly support respective linear transducer arrays for NDI of the sides of the stiffener; the other end of the probe (shown in FIG. 5) is equipped with a pair of transducer assemblies 50c, 50d which compliantly support respective convex curved transducer arrays for NDI of the lower outside radii of the stiffener.

Figure 4:
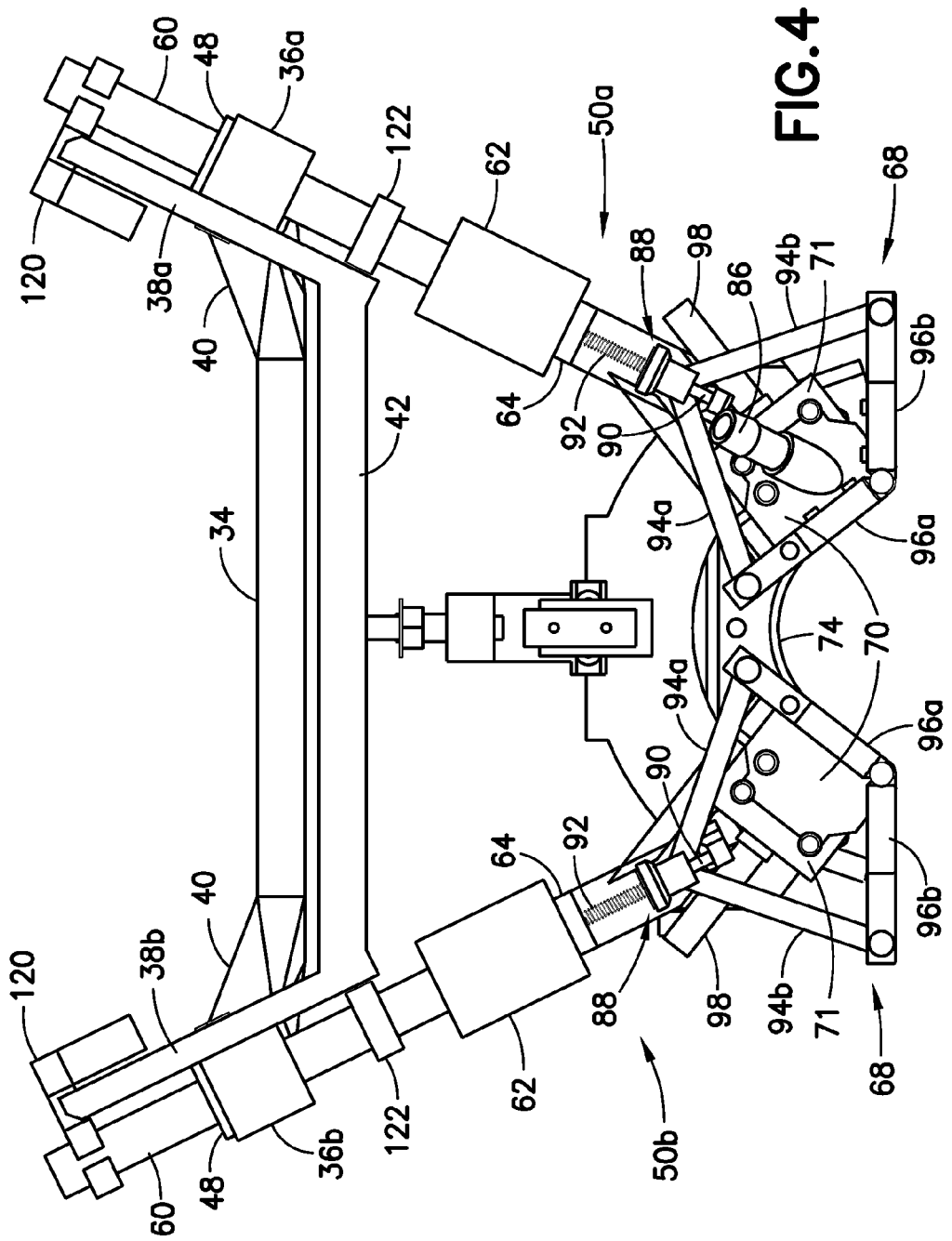
FIGS. 4 and 5 are diagrams representing elevational views of opposite ends of the NDI probe depicted in FIG. 2. One end of the probe comprises a first pair of transducer assemblies compliantly supporting respective linear transducer arrays for NDI of the sides of a stiffener (seen in FIG. 4); the other end of the probe comprises a second pair of transducer assemblies compliantly supporting respective curved transducer arrays for NDI of the lower outside radii of the stiffener (seen in FIG. 5).

Referring to FIG. 4, each of transducer assemblies 50a and 50b further comprises a respective transducer holder 64. Each transducer holder 64 comprises a respective water nozzle connection 86 and a respective shoe 70 that has a respective water column 82 (shown in FIG. 3) formed therein. In accordance with the embodiment shown in FIG. 4, the water nozzle connection and the shoe are integrally formed with other parts of the transducer holder that support the centering mechanism. In the alternative, a transducer holder having a functionally equivalent construction could be assembled from individual components. The water nozzle connection 86 is in fluid communication with the water column, enabling the supply of water to the water column for acoustically coupling a respective linear ultrasonic transducer array 71 to a respective angled side of the stiffener during inspection. The linear transducer arrays 71 are respectively installed inside the shoes 70. The electrical cable connectors 98, which exit from the tops of linear transducer arrays 71, facilitate electrical connection of the respective linear transducer arrays 71 to respective electrical cables (not shown in FIG. 4).

Figure 5:
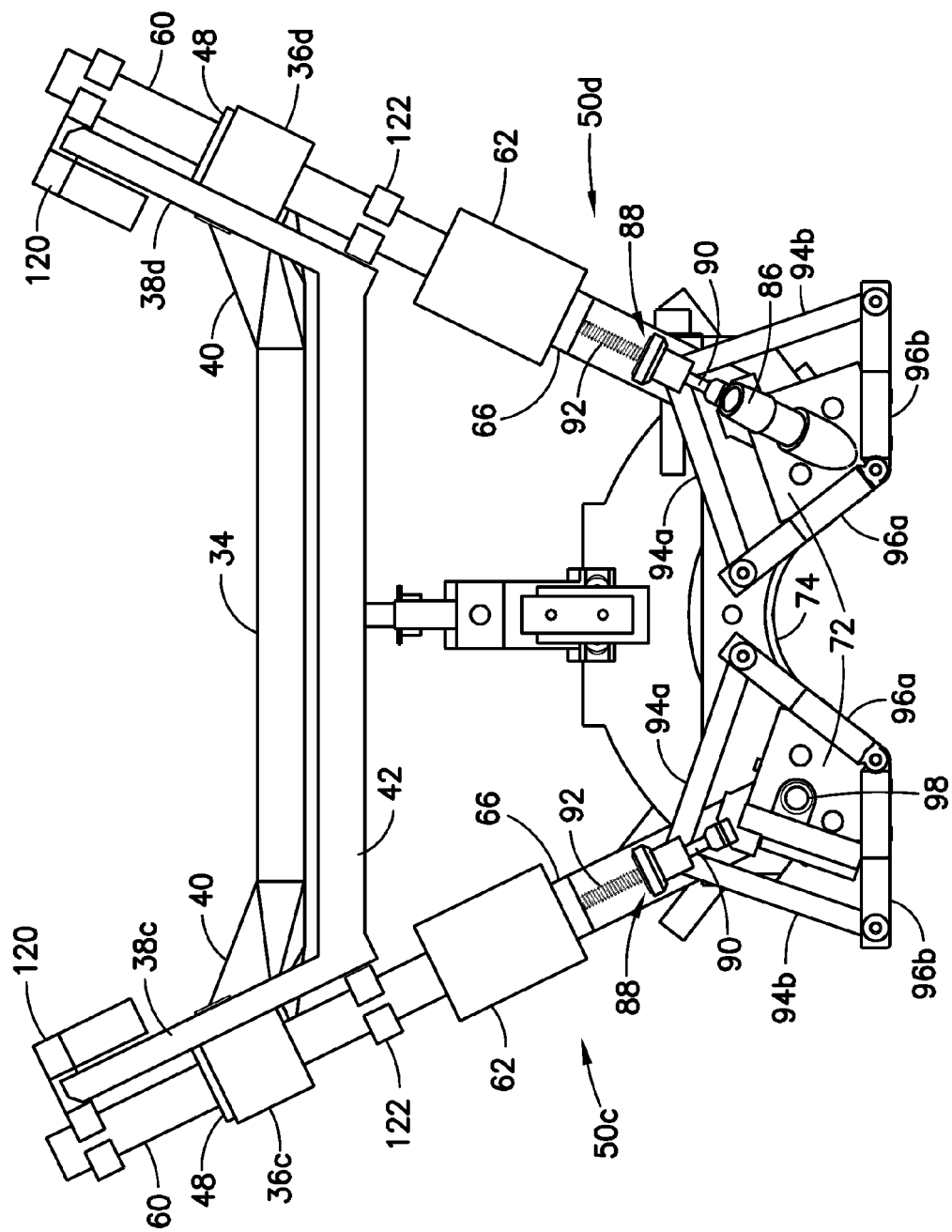

Referring to FIG. 5, each of transducer assemblies 50c and 50d further comprises a respective transducer holder 66. Each transducer holder 66 comprises a respective water nozzle connection 86 and a respective shoe 72 that has a respective water column 84 (shown in FIG. 3) formed therein. The water nozzle connection 86 is in fluid communication with the water column, enabling the supply of water to the water column for acoustically coupling a respective concave curved transducer array (not visible in FIG. 5) to a respective lower outer radius of the stiffener during inspection. A cap and cap latch contain the water in the shoe 72 and reduce water flow. The concave curved transducer arrays are respectively installed inside the shoes 72. The electrical cable connectors 98, which exit the shoes 72 at the sides thereof, facilitate electrical connection of the respective concave curved transducer arrays to respective electrical cables (not shown in FIG. 5).

Referring again to FIG. 2, each of transducer assemblies 50a and 50b further comprises a respective centering mechanism 68 attached to the respective transducer holder 64. In accordance with the implementation shown in FIGS. 4, 7A and 7B, each centering mechanism 68 comprises: first and second small shafts 90 supported at opposite ends thereof by respective mutually opposing cross members of the transducer holder 64; first and second pivot/slide mechanisms 88 slidably coupled to the first and second small shafts 90 respectively; and first and second four-link (94a; 94b, 96a, 96b) centering guide assemblies pivotably coupled to the first and second pivot/slide mechanisms 88 respectively. In addition, the portions of shafts 90 that extend between the uppermost transverse members of a respective transducer holder 64 and a respective pivot/slide mechanism 88 are surrounded by respective compression springs 92, which urge the pivot/slide mechanisms 88 away from the uppermost transverse members of the transducer holders 64.

Figure 7A:
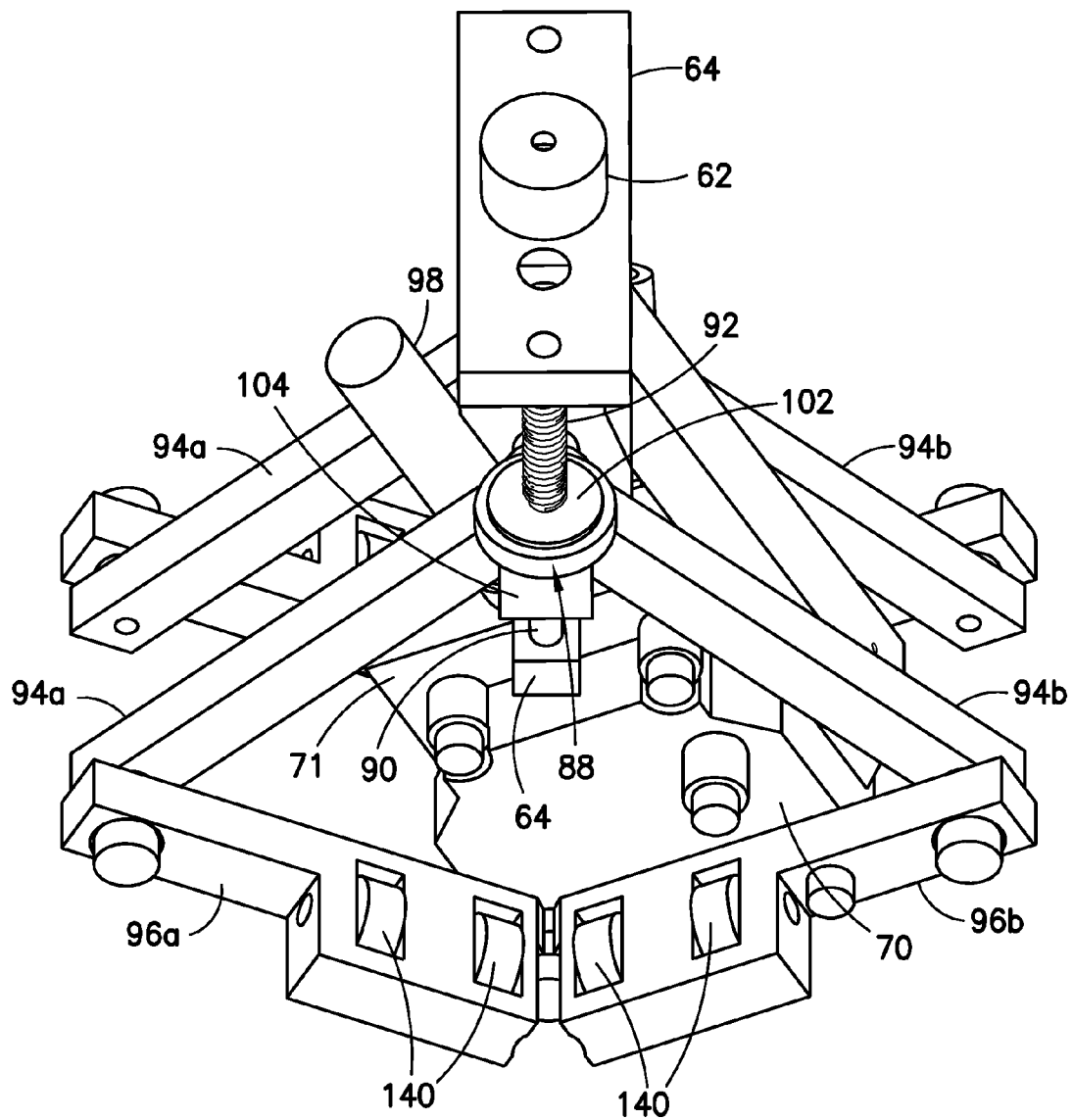
FIGS. 7A and 7B are diagrams representing respective views from different vantage points of the lower portion of an SS transducer assembly in accordance with the embodiment depicted in FIG. 2.
Figure 7B:
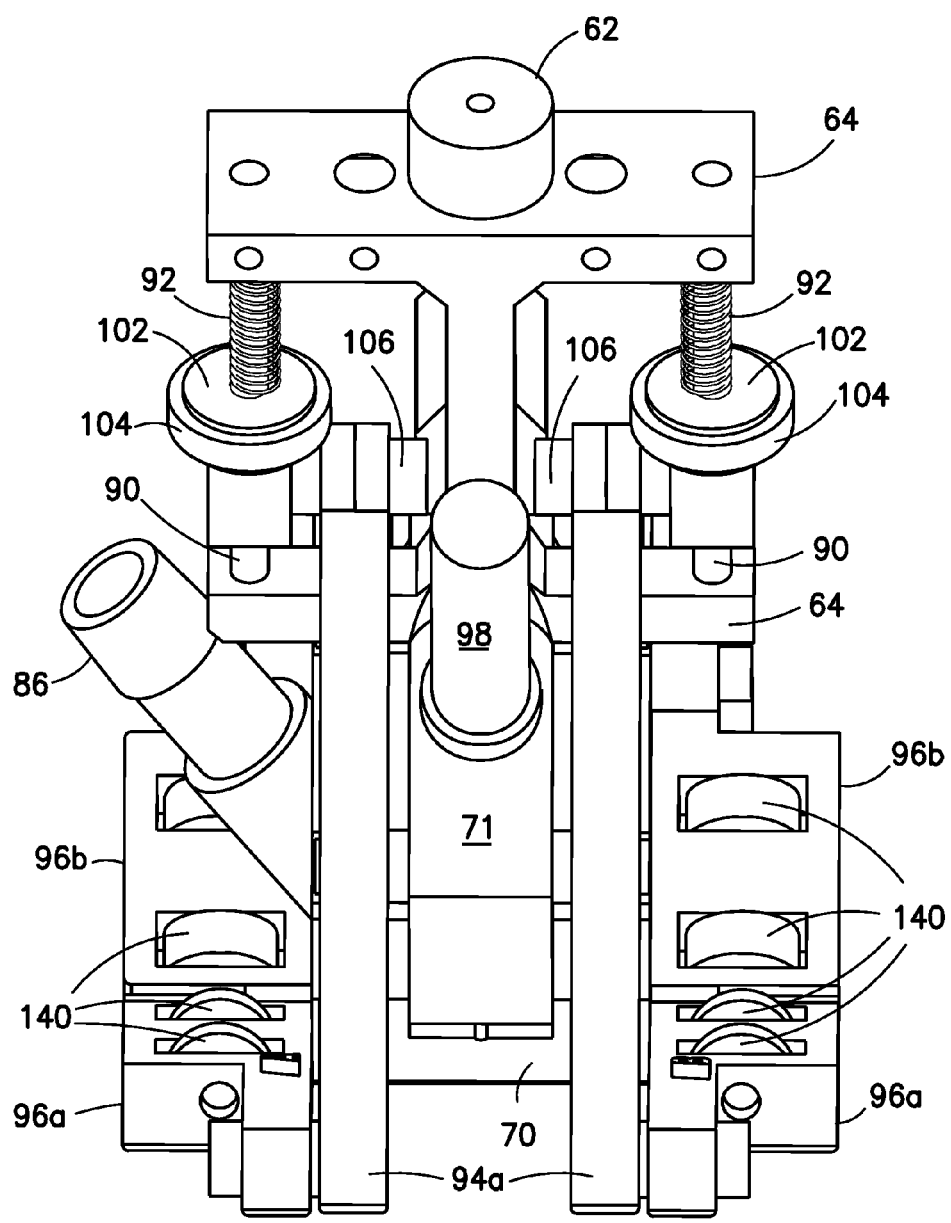

As best seen in FIGS. 7A and 7B, each pivot/slide mechanism 88 comprises a bearing 102, a pivot pin 106 and a bearing support body 104 that supports both the bearing 102 and one end of the pivot pin 106. More specifically, the bearing support body 104 may be fabricated with a first cylindrical bore that has two sections: a first section having a relatively large diameter, in which the bearing 102 is seated, and a second section having a relatively small diameter for passage therethrough of a respective small shaft 90. The bearing support body 104 further comprises a second cylindrical bore that receives one end of a respective pivot pin 106. In one implementation, the axes of the pivot pins 106 are perpendicular to the axes of the shafts 90. In accordance with this construction, each bearing 102 is displaceably coupled to a respective shaft 90, allowing the pivot/slide mechanism 88 to slide up and down along the shaft 90.

Although the pivot/slide mechanism 88 has been described with reference to FIGS. 7A and 7B, which show the lower portions of the transducer assemblies that carry the linear transducer arrays for inspection the stiffener sides, the pivot/slide mechanisms incorporated in the transducer assemblies that carry the convex curved transducer arrays for inspecting the lower outer radii may have the same construction.

FIGS. 7A and 7B also show the structure of the four-link centering guide assemblies of the transducer assemblies that carry the linear transducer arrays. The four-link centering guide assemblies of the transducer assemblies that carry the convex curved transducer arrays for inspecting the lower outer radii have a similar but not identical construction. Each transducer assembly has two four-link centering guide assemblies. The four-link centering guide assemblies for the four transducer assemblies at the four corners of the probe operate on the same principle when the probe is being moved along the length of a stiffener during scanning.

Each four-link centering guide assembly comprises a pair of upper centering guides 94a, 94b and a pair of lower centering guides 96a, 96b. The upper ends of the upper centering guides 94a, 94b are pivotably coupled to a respective pivot pin 106 (see FIG. 7B). The lower ends of the upper centering guides 94a, 94b are respectively pivotably coupled to the upper ends of the lower centering guides 96a, 96b (see FIG. 7A). The lower ends of the lower centering guides 96a, 96b are pivotably coupled to each other (see FIG. 7A). Each linear transducer array 71 is disposed between the first and second four-link centering guide assemblies of a respective transducer assembly. These pivotable couplings produce an adjustable quadrilateral centering structure in which the angle between the lower centering guides 94a and 94b will conform to the angles between the stiffener flanges and angled sides on opposite sides of the stiffener, allowing the transducer array to align with the bisecting angle. The centering mechanisms further comprise respective pluralities of rolling elements 140 rollably coupled to the first and second lower centering guides 96a and 96b (see FIG. 7A). The centering mechanisms provide independent angle alignment in circumstances where the stringer changes angle and/or thickness during probe motion along the length of the stiffener.

Figure 6:
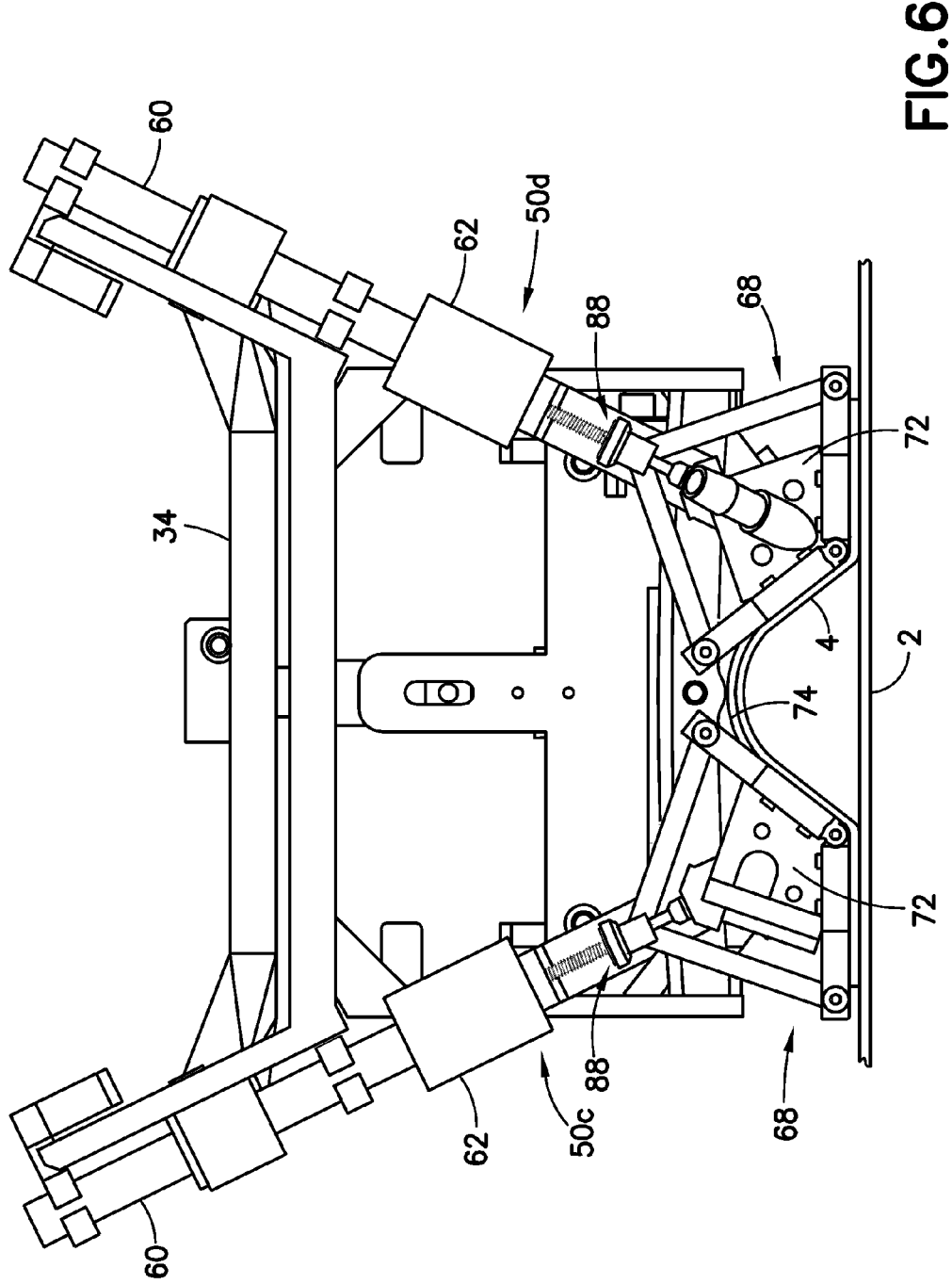
FIG. 6 is a diagram representing the same elevational view presented in FIG. 5 with the addition of the rounded cap stiffener depicted in FIG. 2.

Returning to FIG. 4, the action of the pivot-slide mechanisms 88 allows for variability of the fuselage IML to stringer side angle. This allows for the fuselage's variable radius, as the fuselage is not a constant-radius structure. It is also variable along the length of the fuselage structure. The action of the centering with the pivot/slide mechanism also keeps each linear transducer array in correct position on the respective stringer's side for the SS transducer assemblies 50*a* and 50*b*. This mechanism also keeps each concave curved transducer array of the LOR transducer assemblies 50*c* and 50*d* in alignment with the respective lower outer radius of the stiffener to assure good data coverage, as shown in FIG. 6.

Figure 8:
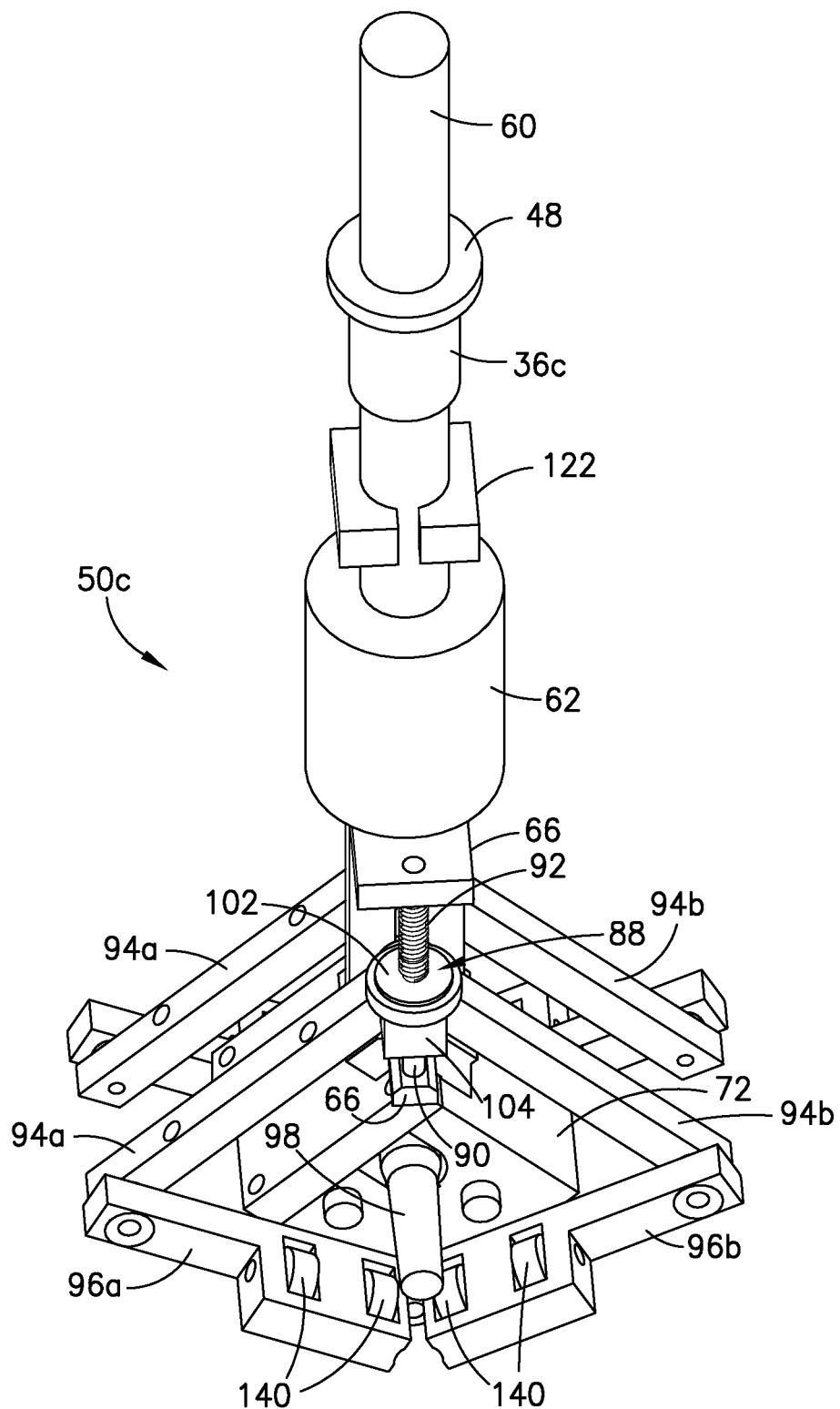
FIG. 8 is a diagram representing one view of an LOR transducer assembly in accordance with the embodiment depicted in FIG. 2.

FIG. 8 shows an LOR transducer assembly 50*c* in accordance with the embodiment depicted in FIG. 2. LOR transducer assembly 50*c* comprises a shaft 60 which is displaceable along and pivotable about its own axis relative to the probe support structure 32 (shown in FIG. 2). The shaft 60 slides and rotates in sleeve bearing 48. The rotation of shaft 60 is limited by a keeper 122, which will hit the probe support structure 32 (see FIG. 2) when the shaft rotation limit (e.g., ±5-10 degrees) is reached. The shaft 60 is coupled to a pair of four-link (94*a*, 94*b*, 96*a*, 96*b*) centering guide assemblies by means of a flexible coupling 62 and a transducer holder 66. The flexure allowed by the flexible coupling 62 accommodates angular, parallel and axial misalignment between the shaft 60 and the transducer holder 66.

Referring back to FIG. 2, the axial displacement of each shaft 60 is measured by a respective linear position sensor 124 which is affixed to a respective support leg 38*a*-38*d*. The linear position sensor 124 may take the form of a soft potentiometer. A respective accessory part 120, having a pressure contact point threaded into a hole formed therein, is attached to the upper end of the respective shaft 60. Each linear position sensor 124 senses the distance traveled by the pressure contact point of a respective accessory part 120.

Figure 12:
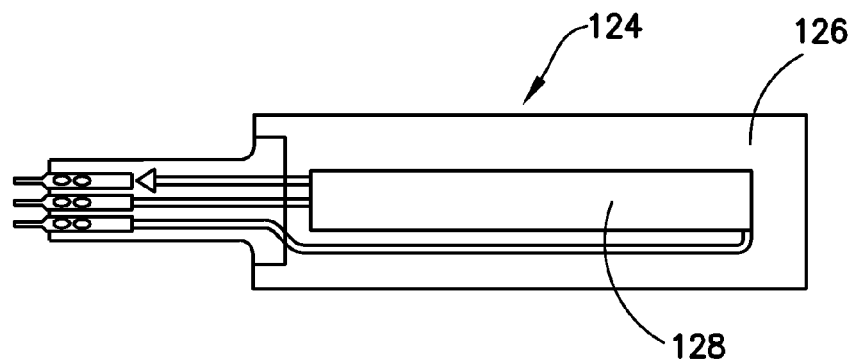
FIG. 12 is a diagram representing a top view of a linear position sensor. Four such linear position sensors are attached to the probe support structure for detecting displacements of transducer assemblies relative to the probe support structure.

As shown in FIG. 12, the linear position sensor 124 is a three-wire system with two resistive output channels and an electrical collector current on a polyester substrate 126. By pressing a pressure contact point down onto the top circuit 128, the linear position sensor 124 produces an electrical output indicative of the linear position of the pressure contact point. Since the pressure contact point is affixed to the shaft, the sensor output also indicates the axial displacement of the shaft.

Figure 13A:
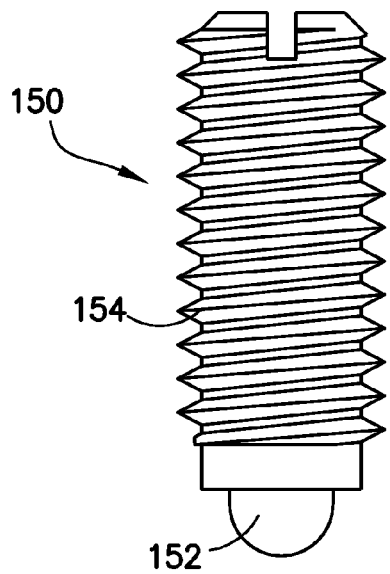
FIG. 13A is a diagram representing an elevational view of a pin actuator which is used in conjunction with the linear position sensor depicted in FIG. 12.
Figure 13B:
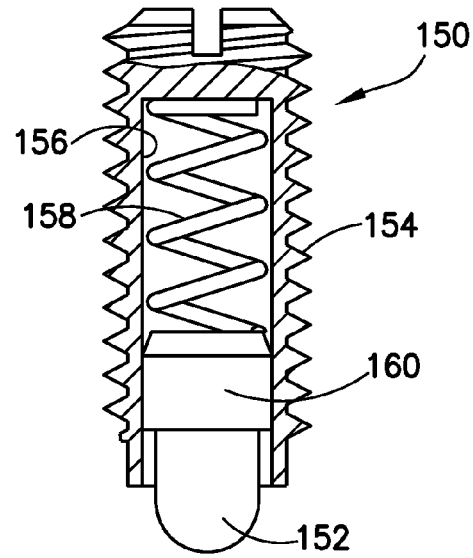
FIG. 13B is a diagram representing a cross-sectional view of the pin actuator depicted in FIG. 13A.

In accordance with one embodiment, the pressure contact point takes the form of a pin actuator 150 shown in FIGS. 13A and 13B. The pin actuator 150 comprises a housing having outer threads 154 and a circular cylindrical bore 156. The pin comprises a plug 160 which is slidable in bore 156 and a rounded tip 152 which protrudes from the housing and contacts the linear position sensor. As the shaft displaces axially, the rounded tip 152 bears against the top circuit 128 (see FIG. 12), producing sensor output signals indicative of incremental axial displacement of the shaft. The axial displacement of each shaft 60 (see FIG. 2) can be detected in this manner.

During set-up, the pressure of the respective spring (not shown) that surrounds a portion of each shaft can be adjusted in dependence on the outputs of the linear position sensors. Each spring can be selected with a different spring constant as well as length to get an optimum setting and position of each shaft, i.e., the position of the probe on the stringer.

Figure 9:
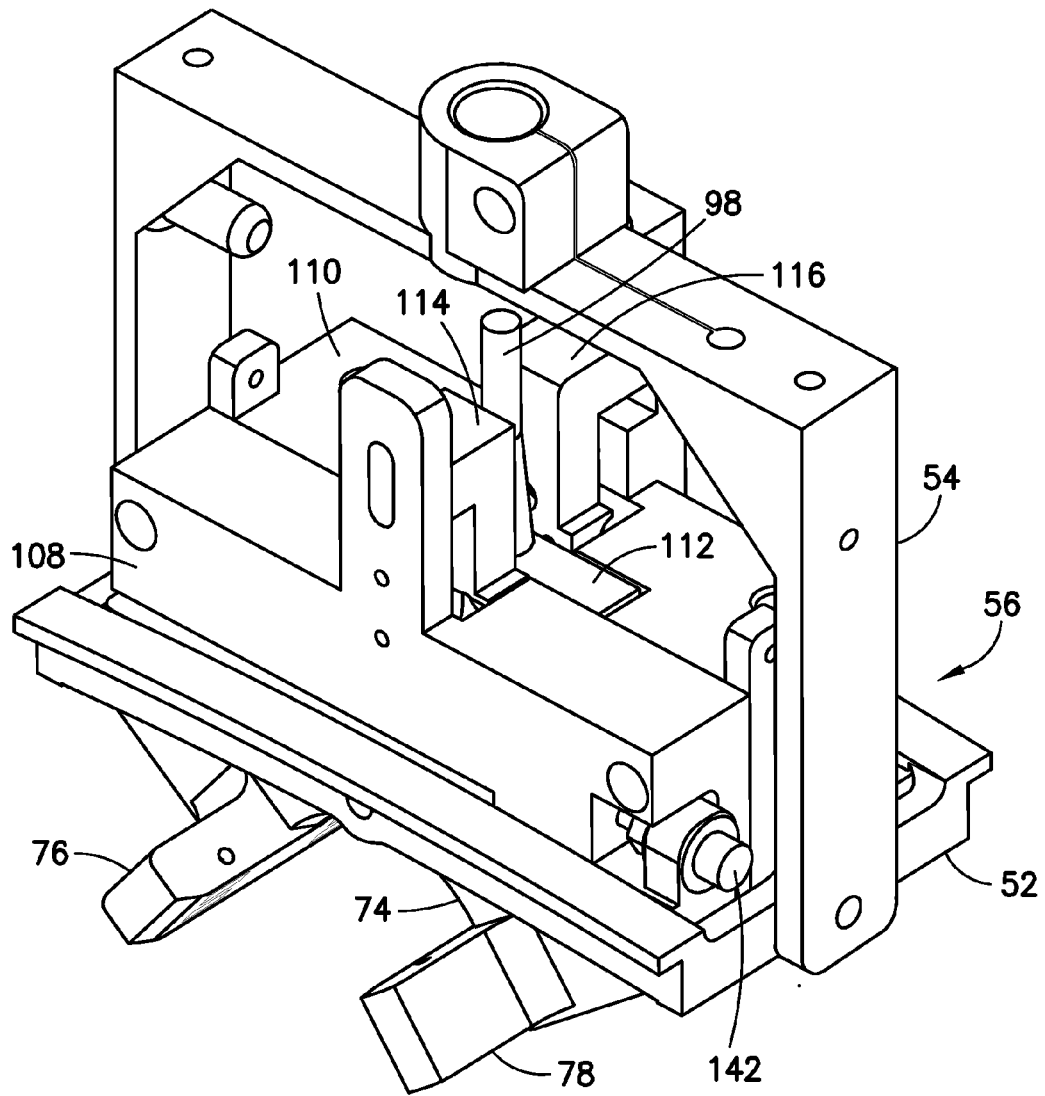
FIG. 9 is a diagram representing one view of a UCR transducer assembly pivotably coupled to a yoke in accordance with the embodiment depicted in FIG. 2.

In addition to inspecting the angled sides and lower outer radii of the stringer, the probe 18 shown in FIG. 2 is capable of concurrently inspecting the rounded cap of the stringer. FIG. 9 shows various components of a UCR transducer assembly in accordance with one embodiment. The UCR transducer assembly is supported by a yoke 56 comprising a cradle 52 attached to a cross bar 54. The yoke 56 (seen in FIG. 9) and the main structure plate 34 (seen in FIG. 2) are both connected to a robot interface plate/assembly (not shown). The robot interface plate/assembly is disposed at a distal end of a robot end effector (described later with reference to FIG. 14).

The UCR transducer assembly comprises a lower housing 74 (previously described with reference to FIG. 5) that has roller bearings on respective inner surfaces for sliding across the stringer's cap. The UCR transducer assembly further comprises an upper housing (parts 108 and 110) that is coupled to the lower housing 74. The upper housing can be moved transversely relative to the lower housing by means of a bolt 142 which is threadably coupled to a flange that projects upward from the lower housing 74.

Figure 10:
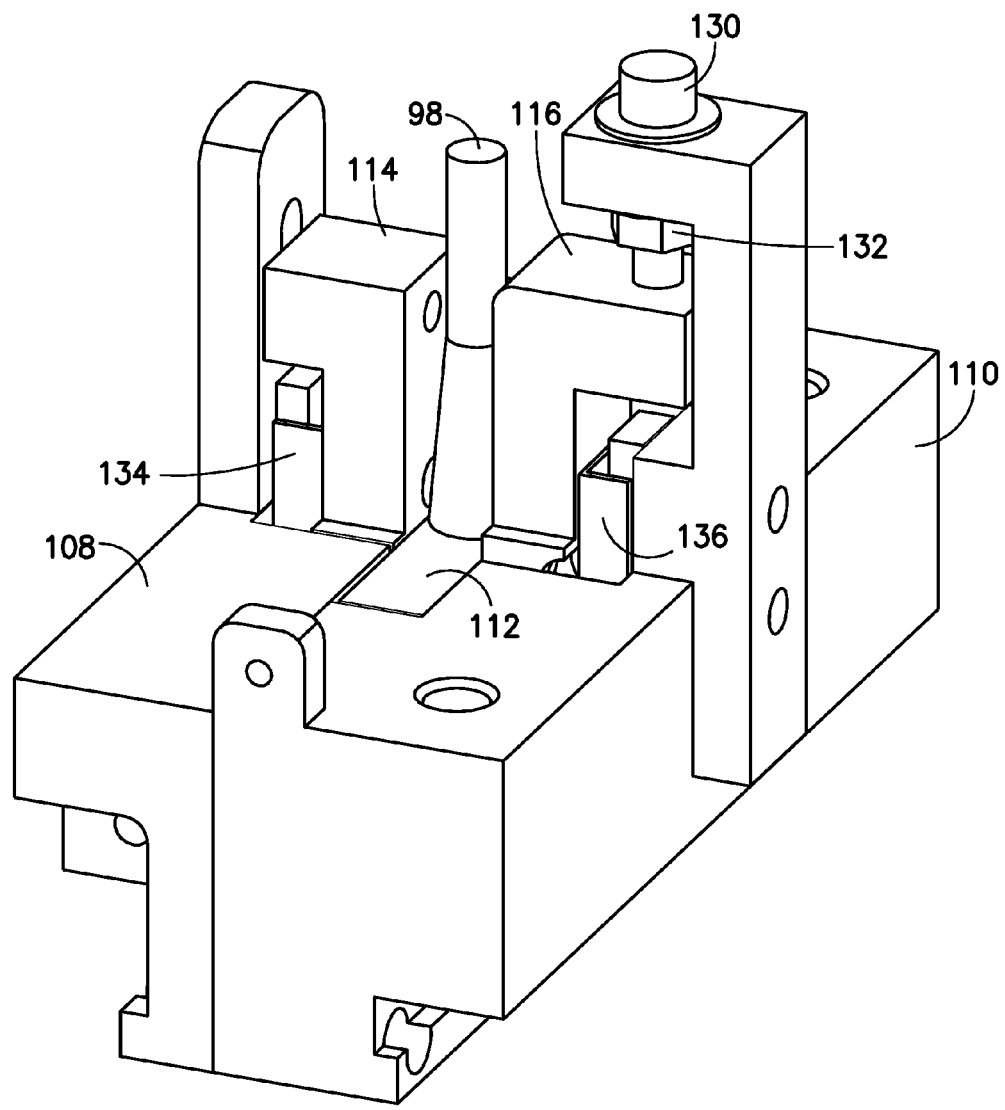
FIG. 10 is a diagram representing one view of the UCR transducer assembly depicted in FIG. 2, but with a lower housing (see in FIG. 3) of the UCR transducer assembly omitted.
Figure 11:
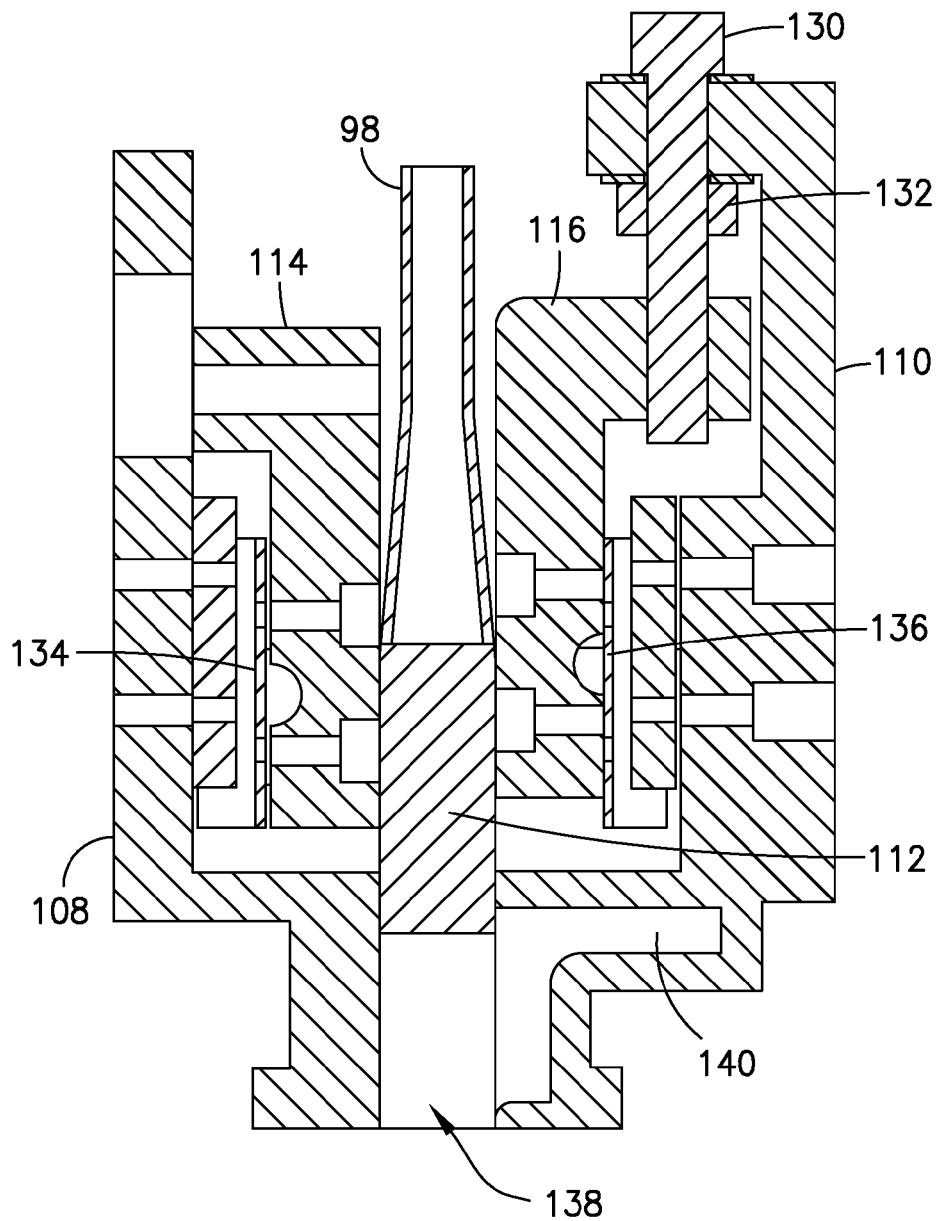
FIG. 11 is a diagram representing a cross-sectional view of the structure seen in FIG. 10.

As best seen in FIGS. 10 and 11, a convex curved transducer array 112 is attached to and between two fixture components 114 and 116 which are slidable relative to the upper housing parts 108 and 110 respectively by means of respective sliders 134 and 136. This allows the vertical position of the transducer array 112 to be adjusted. Stainless steel sliders are used to provide low hysteresis and exacting alignment. The lower portions of the upper housing parts 108 and 110 form a water column 138, which connects to a source of water by a manifold 140 formed in upper housing part 110. The transducer array 112 projects into the water column 138, which is filled with water during inspection of the rounded cap of the stringer.

In accordance with the embodiment shown in FIG. 11, the vertical position of the transducer array 112 can be manually adjusted by turning a bolt 130 which has an unthreaded portion in an unthreaded bore formed in the upper housing part 110 and a threaded portion in a threaded bore formed in the fixture component 116.

In accordance with an alternative embodiment, the adjustment of the vertical position of the transducer array 112 could be automated by replacing the bolt 130 with a motor-driven lead screw, as taught in U.S. Pat. No. 8,082,793, the disclosure of which is incorporated by reference herein in its entirety.

In accordance with one implementation, the convex curved transducer array for NDI of the rounded cap of the stringer may be a two-inch 64-element curved array with cylindrical focus; the linear transducer arrays for NDI of the stringer sides may be 16-element flat linear arrays; and the concave curved transducer arrays for NDI of the lower outer radii of the stringer may be 16-element radius arrays having a radius of 10.2 mm and an angle of 90 degrees. The first two types of arrays are commercially available from GE Inspection Technologies; the third type of array is commercially available from Olympus.

Figure 14:
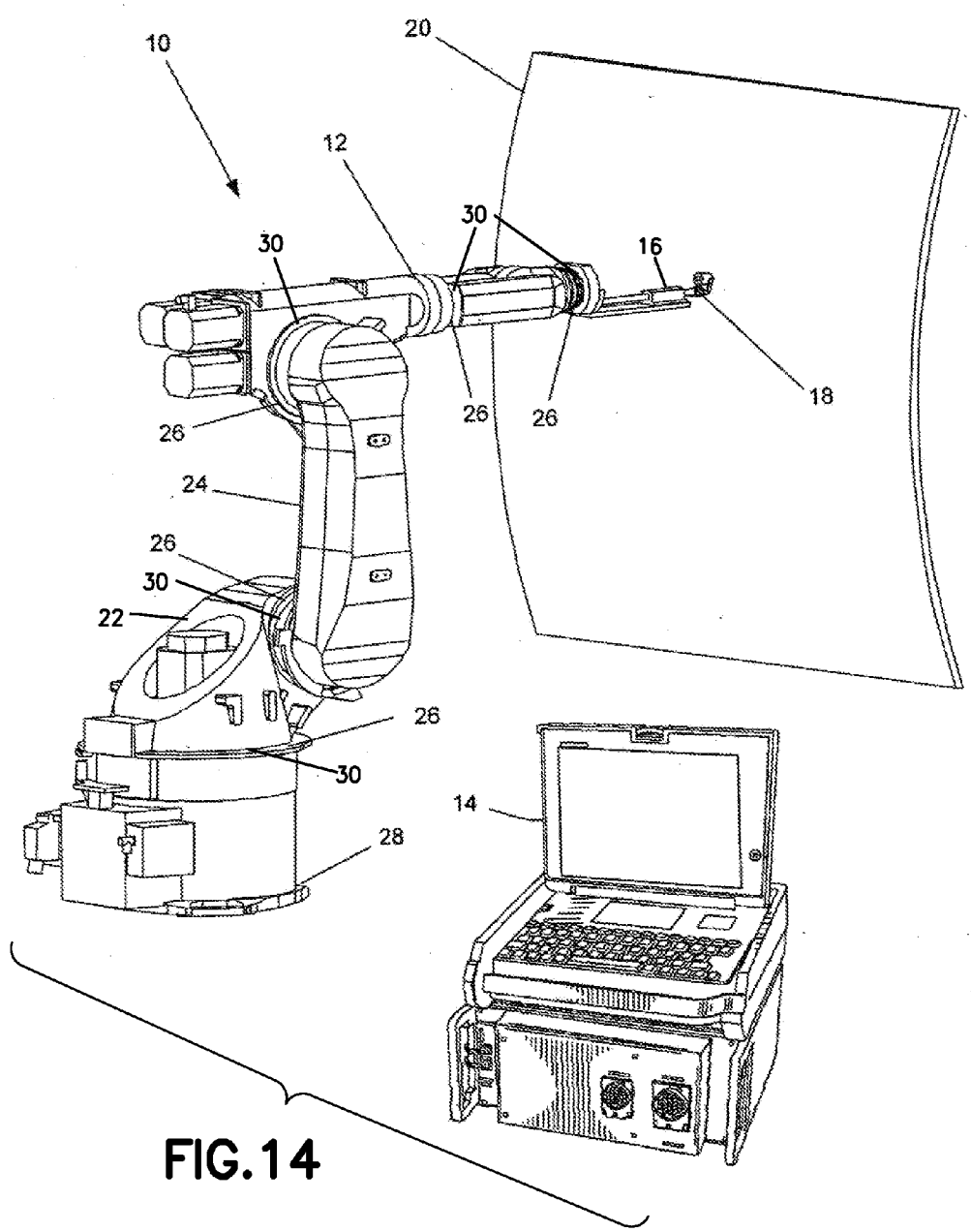
FIG. 14 is a perspective view of a non-destructive inspection system comprising a probe that is carried by a robot and in communication with a data acquisition system in accordance with one embodiment.

FIG. 14 shows an inspection system for inspecting a structure 20 (e.g., a fuselage). The inspection system comprises a robot 10, a data acquisition system 14, and a probe 18 that is mounted to a robot end effector 16 disposed at the end of a robot arm 12 and in communication with the data acquisition system 14. (In other words, the probe 18 is coupled to the robot arm 12 by means of the robot end effector 16.) As the probe 18 is moved along the structure 20, data is sent to the data acquisition system 14 for processing. Typically, the robot 10 is automatically controlled to move the probe 18 in proximity to the structure 20, while the data acquisition system 14 generates images of the surface of the structure 20 to map the probe's response. The robot 10 could be used to inspect any number of structures in a variety of industries where detection of flaws or defects in the structure is required, such as in the aircraft, automotive, or construction industries. In particular, if the probe 18 is of the type shown in FIG. 2, the robot 10 could be used to inspect stiffeners of the type shown in FIGS. 1 and 2.

The robot 10 has multi-axis movement capabilities and uses software support to generate a three-dimensional profile to be used for measurement and inspection of parts. In particular, the robot 10 shown in FIG. 14 comprises a base 28, a carrousel 22, a rocker 24, a robot arm 12 and an end effector 16, which components are rotatably coupled by a plurality of pivots 26. The combination of these components provides several degrees of freedom, which in turn, allows the probe 18 to be moved to different locations and in different directions. The robot 10 includes one or more positional sensors 30 at, or otherwise associated with, each of the pivots 26 that provide positional data (X, Y, and Z in three-dimensional space) to the data acquisition system 14 for accurately locating the probe 18, as disclosed in U.S. Pat. No. 7,448,271 (the disclosure of which is incorporated by reference herein). For example, the robot 10 shown in FIG. 14 includes six pivots 26, where each pivot includes a positional encoder 30 that collectively defines the three-dimensional location of the probe 18. The probe 18 provides NDI data indicative of the structure 20. As such, the robot 10 provides an accurate location of any defects using positional data and NDI data acquired during inspection of the structure 20.

An example of a robot 10 that could be employed with the probe shown in FIG. 2 is robot Model KR-150 manufactured by Kuka Roboter GmbH (Augsburg, Germany), although any robot or other manipulator capable of carrying a probe 18 and communicating with a data acquisition system 14 could be used. Furthermore, the robot 10 could include various numbers of sensors 30 (e.g., one or more) for acquiring positional data, and the sensors 30 could be located at different locations, such as proximate to probe 18.

The data acquisition system 14 is capable of generating various images, including A-scan, B-scan, and C-scan images of complex-shaped structures 20 based on data collected by the positional sensors 30 and probe 18. Furthermore, the data acquisition system 14 is capable of generating a three-dimensional point cloud based on the data acquired by the positional sensors 30 and probe 18. Thus, a stream of positional data may be mapped to a stream of NDI data to generate the point cloud. The NDI data may include, among other information, data regarding defects, irregularities, or other imperfections in the structure 20.

The data acquisition system 14 typically includes a processor or similar computing device operating under the control of imaging software so that any defects in the structure 20 may be presented on a display. The processor could be embodied by a computer such as a desktop, laptop, or portable processing device capable of processing the data generated by the positional sensors 30 and probe 18 and creating an image of the scanned data that is shown on a display such as a monitor or other viewing device. The data acquisition system 14 generates images of the data and also allows a user to store and edit previously created images. Therefore, a permanent record of the images may be kept for future use or record keeping. However, it is understood that the data acquisition system 14 need not generate images, as the data acquisition system could mathematically collect and analyze positional and NDI data that a technician could use to characterize and locate a flaw based on the data.

The robot 10 is typically in communication with the data acquisition system 14 to process the data accumulated by the positional sensors 30 and probe 18 and to display the processed data. In many cases, communications cable(s) (not shown in FIG. 14) transmit data between the robot 10 and the data acquisition system 14. In other embodiments, the data may be transmitted between the robot 10 and the data acquisition system 14 via wireless communications. The robot 10 may be directly connected to the processor, or indirectly connected, such as via a network. In further embodiments, the data acquisition system 14 may be located proximate to the robot 10, such that remote connections between the robot and data acquisition system are not necessary. Moreover, it is understood that data acquisition system 14 could be incorporated with the robot 10 such that the data is collected and processed by the robot.

Other types of end effector positioning systems may be used, including combinations of linear Cartesian axis platforms, rotary axis platforms, and Stewart platforms using parallel kinematics. Specific examples include gantries, other types of robots, robots-on-rail, post-mill type platforms, and Stewart platforms (e.g. hexapods). In each of these examples, the end effector positioning system is configured to deliver a selected end effector to a position or along a path to perform its function, while satisfying performance requirements (e.g., angles, velocity, acceleration, stiffness, range of travel, utilities, quick-release coupling).

Figure 15:
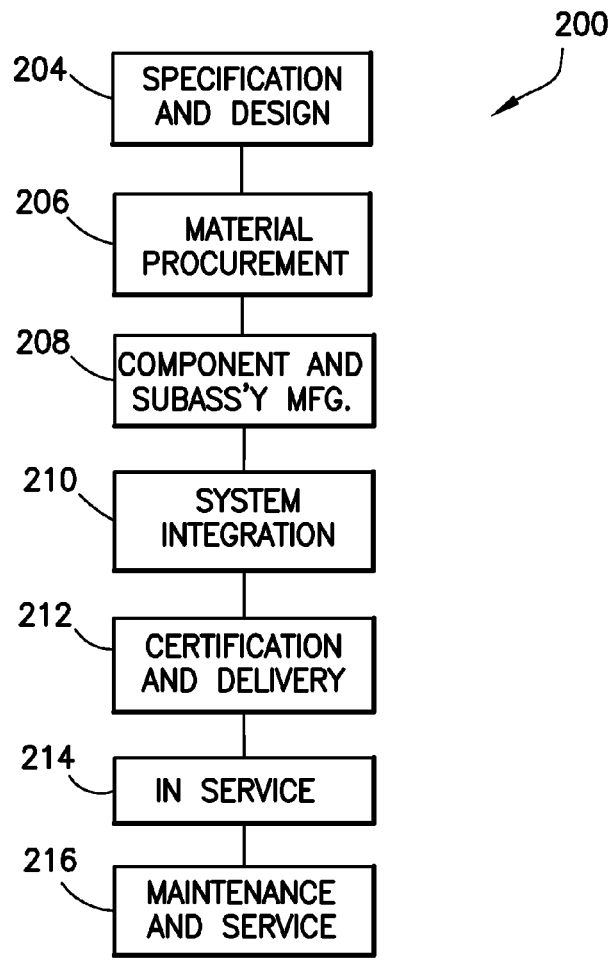
FIG. 15 is a flow diagram of an aircraft production and service methodology.
Figure 16:
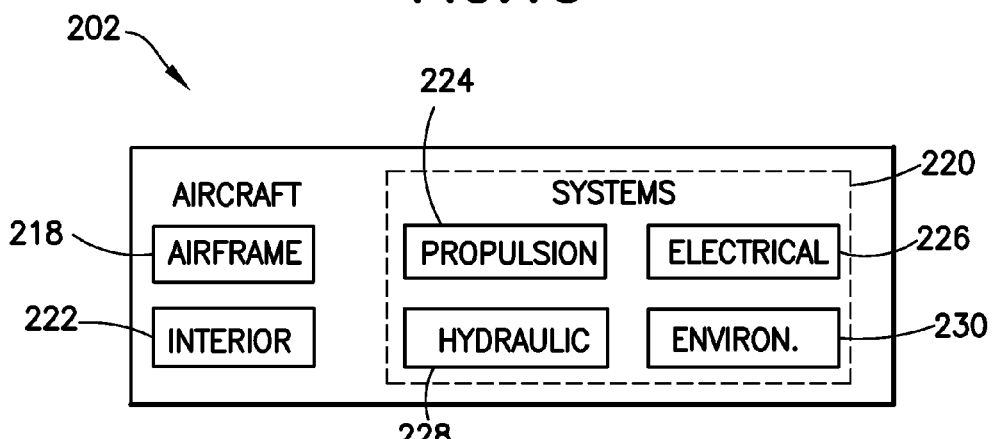
FIG. 16 is a block diagram showing systems of an aircraft.

The system and method disclosed above may be employed in an aircraft manufacturing and service method 200 as shown in FIG. 15 for inspecting parts of an aircraft 202 as shown in FIG. 16. During pre-production, exemplary method 200 may include specification and design 204 of the aircraft 202 and material procurement 206. During production, component and subassembly manufacturing 208 and system integration 210 of the aircraft 202 takes place. Thereafter, the aircraft 202 may go through certification and delivery 212 in order to be placed in service 214. While in service by a customer, the aircraft 202 is scheduled for routine maintenance and service 216 (which may also include modification, reconfiguration, refurbishment, and so on).

Each of the processes of method 200 may be performed or carried out by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

As shown in FIG. 16, the aircraft 202 produced by exemplary method 200 may include an airframe 218 (comprising, e.g., a fuselage, frames, stiffeners, wing boxes, etc.) with a plurality of systems 220 and an interior 222. Examples of high-level systems 220 include one or more of the following: a propulsion system 224, an electrical system 226, a hydraulic system 226, and an environmental control system 230. Any number of other systems may be included. Although an aerospace example is shown, the principles disclosed herein may be applied to other industries, such as the automotive industry.

Apparatus and methods embodied herein may be employed during any one or more of the stages of the production and service method 200. For example, components or subassemblies fabricated or assembled during production process 208 may be inspected using the inspection system disclosed herein. Also, one or more apparatus embodiments, method embodiments, or a combination thereof may be utilized during the production stages 208 and 210, for example, by substantially expediting assembly of or reducing the cost of an aircraft 202. Similarly, one or more of apparatus embodiments, method embodiments, or a combination thereof may be utilized while the aircraft 202 is in service, for example and without limitation, during maintenance and service 216.

While NDI probes have been described with reference to various embodiments, it will be understood by those skilled in the art that various changes may be made and equivalents may be substituted for elements thereof without departing from the scope of the teachings herein. In addition, many modifications may be made to adapt the teachings herein to a particular situation without departing from the scope thereof. Therefore it is intended that the claims not be limited to the particular embodiments disclosed herein.

The invention claimed is:

1. An apparatus comprising:
a support structure;
a first large shaft pivotably and slidably coupled to said support structure;
a first flexible coupling attached to one end of said first large shaft;
a first transducer holder attached to said first flexible coupling;
a first transducer array supported by said first transducer holder; and
a first centering mechanism attached to said first transducer holder,
wherein said first centering mechanism comprises first and second adjustable quadrilateral centering guide assemblies.

2. The apparatus as recited in claim 1, wherein said first centering mechanism further comprises:
first and second small shafts supported at opposite ends thereof by said first transducer holder; and
first and second pivot/slide mechanisms slidably coupled to said first and second small shafts respectively,
wherein said first and second adjustable quadrilateral centering guide assemblies are pivotably coupled to said first and second pivot/slide mechanisms respectively.

3. The apparatus as recited in claim 2, wherein said first pivot/slide mechanism comprises a first bearing and a first pivot pin, and said second pivot/slide mechanism comprises a second bearing and a second pivot pin, said first and second small shafts being slidable in said first and second bearings respectively, and said first and second adjustable quadrilateral centering guide assemblies being pivotably coupled to said first and second pivot pins respectively.

4. The apparatus as recited in claim 2, wherein each of said first and second adjustable quadrilateral centering guide assemblies comprises first and second upper centering guides pivotably coupled to said first and second pivot/slide mechanisms respectively and first and second lower centering guides respectively pivotably coupled to said first and second upper centering guides and pivotably coupled to each other.

5. The apparatus as recited in claim 4, wherein said first centering mechanism further comprises respective pluralities of rolling elements rollably coupled to said first and second lower centering guides.

6. The apparatus as recited in claim 2, wherein said transducer array is disposed between said first and second adjustable quadrilateral centering guide assemblies.

7. The apparatus as recited in claim 1, further comprising:
a second large shaft pivotably and slidably coupled to said support structure;
a second flexible coupling attached to one end of said second large shaft;
a second transducer holder attached to said second flexible coupling;
a second transducer array held by said second transducer holder; and
a second centering mechanism attached to said second transducer holder,
wherein said second centering mechanism comprises third and fourth adjustable quadrilateral centering guide assemblies.

8. The apparatus as recited in claim 7, wherein said first transducer array has a concave curvature, said second transducer array is linear, and said first and second transducer arrays are arranged so that when said first transducer array confronts a lower outer radius of a stiffener, said second transducer array will confront a side of the stiffener.

9. The apparatus as recited in claim 7, wherein each of said first and second transducer arrays has a concave curvature, and said first and second transducer arrays are arranged so that when said first transducer array confronts a first lower outer radius of a stiffener, said second transducer array will confront a second lower outer radius of the stiffener.

10. The apparatus as recited in claim 7, wherein each of said first and second transducer arrays is linear, and said first and second transducer arrays are arranged so that when said first transducer array confronts a first side of a stiffener, said second transducer array will confront a second side of the stiffener.

11. An apparatus comprising:
a first support structure having an axis, said first support structure comprising a plate disposed perpendicular to said axis and first through fourth sleeves fixedly coupled to said plate and disposed at respective corners of a rectangle;
first through fourth bearings seated in said first through fourth sleeves respectively;
first through fourth large shafts pivotably and displaceably coupled to said first through fourth bearings respectively;
first through fourth flexible couplings respectively attached to respective ends of said first through fourth large shafts;
first through fourth transducer holders respectively attached to said first through fourth flexible couplings;
first through fourth transducer arrays respectively attached to said first through fourth transducer holders; and
first through fourth centering mechanisms respectively attached to said first through fourth transducer holder,
wherein each of said first through fourth centering mechanism comprises a respective pair of adjustable quadrilateral centering guide assemblies.

12. The apparatus as recited in claim 11, wherein each of said first through fourth centering mechanisms further comprises:
first and second small shafts supported at opposite ends thereof by a respective one of said first through fourth transducer holders; and
first and second pivot/slide mechanisms slidably coupled to said first and second small shafts respectively,
wherein each pair of adjustable quadrilateral centering guide assemblies comprises first and second adjustable quadrilateral centering guide assemblies pivotably coupled to said first and second pivot/slide mechanisms respectively.

13. The apparatus as recited in claim 12, wherein each of said first pivot/slide mechanisms respectively comprises a first bearing and a first pivot pin, and each of said second pivot/slide mechanisms respectively comprises a second bearing and a second pivot pin, said first and second small shafts being slidable in said first and second bearings respectively, and said first and second adjustable quadrilateral centering guide assemblies being pivotably coupled to said first and second pivot pins respectively.

14. The apparatus as recited in claim 12, wherein each of said first and second adjustable quadrilateral centering guide assemblies comprises first and second upper centering guides pivotably coupled to said first and second pivot/slide mechanisms respectively and first and second lower centering guides respectively pivotably coupled to said first and second upper centering guides and pivotably coupled to each other.

15. The apparatus as recited in claim 12, wherein said first through fourth transducer arrays are respectively disposed between a respective pair of said first and second adjustable quadrilateral centering guide assemblies.

16. The apparatus as recited in claim 11, wherein each of said first and second transducer arrays has a concave curvature, each of said third and fourth transducer arrays is linear, and said first through fourth transducer arrays are arranged so that when said first transducer array confronts a first outer radius of a stiffener, said second transducer array will confront a second outer radius of the stiffener, said third transducer array will confront a first side of the stiffener, and said fourth transducer array will confront a second side of the stiffener.

17. The apparatus as recited in claim 16, further comprising:
- a second support structure fixedly coupled to said first support structure;
- a fifth transducer holder pivotably coupled to said second support structure; and
- a fifth transducer array held by said fifth transducer holder, wherein said fifth transducer array has a concave curvature of sufficient length to enable interrogation of a rounded cap of the stiffener when said first transducer array confronts the first outer radius of the stiffener.

\* \* \* \* \*